United States Patent
Lacoux

(10) Patent No.: US 7,132,269 B2
(45) Date of Patent: Nov. 7, 2006

(54) COUPLING AGENTS, THE ACTIVE INTERMEDIATES AND THE CONJUGATES THEREOF AND THE USE OF SAID CONJUGATES IN DIAGNOSTIC METHODS

(75) Inventor: Xavier Lacoux, Dommartin (FR)

(73) Assignee: Biomerieux, Marcy l'Etoile (FR)

( * ) Notice: Subject to any disclaimer, the term of this patent is extended or adjusted under 35 U.S.C. 154(b) by 0 days.

(21) Appl. No.: 10/505,746

(22) PCT Filed: Feb. 26, 2003

(86) PCT No.: PCT/FR03/00619

§ 371 (c)(1),
(2), (4) Date: May 27, 2005

(87) PCT Pub. No.: WO03/072546

PCT Pub. Date: Sep. 4, 2003

(65) Prior Publication Data

US 2005/0215771 A1    Sep. 29, 2005

(30) Foreign Application Priority Data

Feb. 28, 2002   (FR) .................... 02 02559

(51) Int. Cl.
  *C12N 9/96*    (2006.01)
  *C07D 207/448* (2006.01)
  *G01N 33/553*  (2006.01)
  *G01N 33/545*  (2006.01)
  *C07K 1/13*    (2006.01)

(52) U.S. Cl. ................ 435/188; 435/6; 435/7.5; 435/7.92; 546/521; 436/544; 436/545; 436/546; 530/395; 530/409

(58) Field of Classification Search ............... 548/521; 530/409, 395; 435/188, 6, 7.5, 7.92, 974; 436/544, 545, 546

See application file for complete search history.

(56) References Cited

U.S. PATENT DOCUMENTS 5,162,505 A    11/1992   Dean et al.
5,929,211 A    7/1999    Ashkenazi et al.

FOREIGN PATENT DOCUMENTS

WO    WO 99/13919    3/1999

OTHER PUBLICATIONS

Stephen D. Mikolajczyk, et al., "High Yield, Site-Specific Coupling of N-Terminally Modified beta-Lactamase to a Proteolytically Derived Single-Sulfhydryl Murine Fab", Bioconjugate Chem., 1994, 5, pp. 636-646.
Pierce Catalog, Pierce Chemical Company, Jan. 1999; EMCH, KMUH, MPBH, BMPH.

*Primary Examiner*—Mary E. Ceperley
(74) *Attorney, Agent, or Firm*—Clark & Brody

(57) ABSTRACT

The present invention concerns coupling agents having the following general formula:

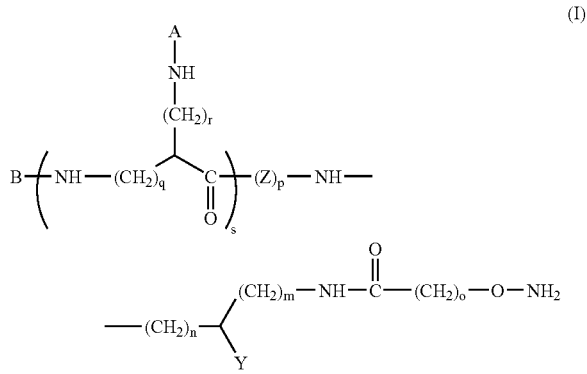

activated intermediates consisting of a coupling agent such as defined above with either a molecule having on its surface at least one aldehyde and/or ketone function before conjugation, or with one to eight molecules having on their surface at least one free thiol function before conjugation, conjugates consisting of a coupling agent such as defined above, of a molecule having on its surface at least one aldehyde and/or ketone function and of one to eight molecules having on their surface at least one free thiol function, and the use of said conjugates for in vitro diagnostic methods of diseases involving recognition of a ligand-antiligand pair.

29 Claims, 1 Drawing Sheet

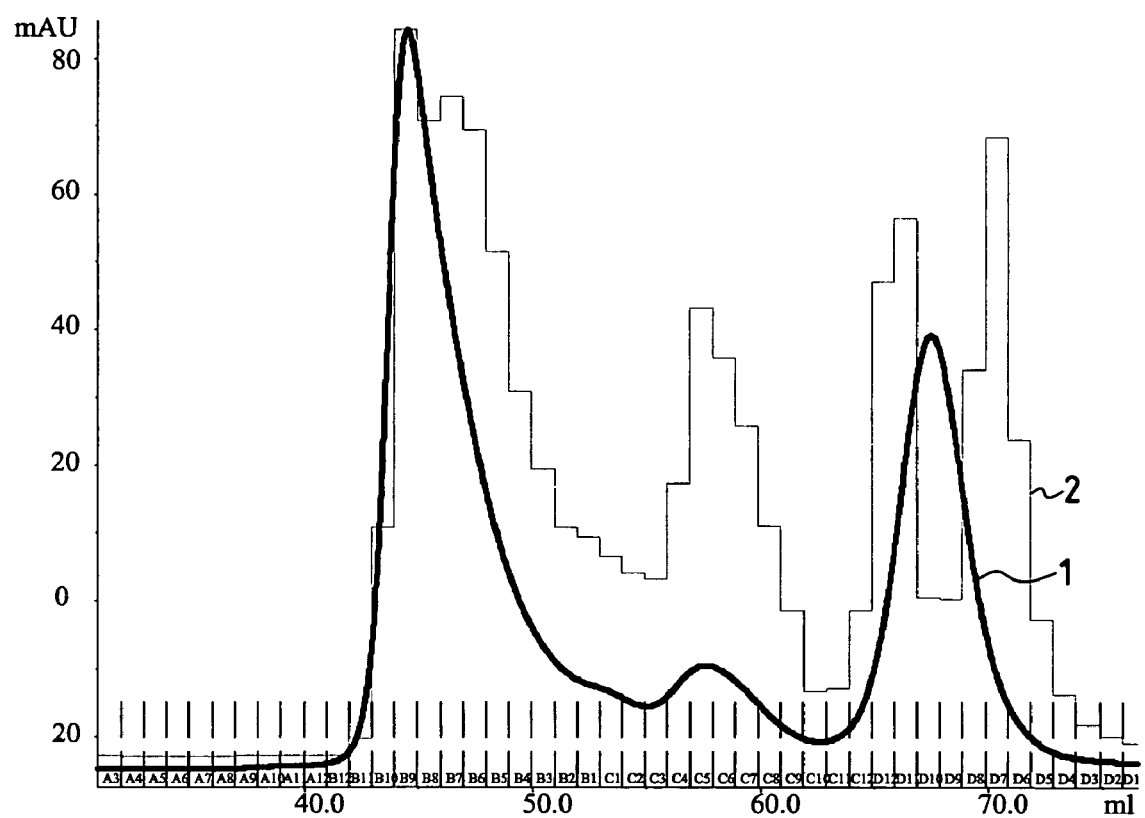

COUPLING AGENTS, THE ACTIVE INTERMEDIATES AND THE CONJUGATES THEREOF AND THE USE OF SAID CONJUGATES IN DIAGNOSTIC METHODS

FIELD OF INVENTION

The present invention concerns heterobifunctional coupling agents which may be used in particular for the coupling of molecules having on their surface at least one aldehyde and/or ketone function and molecules having on their surface at least one free thiol function.

BACKGROUND OF INVENTION

Coupling agents are useful in the area of diagnosis, in particular to detect reactions of ligand-anti-ligand type such as antigen-antibody or protein-protein, since they allow the direct coupling of a molecule of biological interest, such as an antigen, with a detecting molecule such as an enzyme. The binding of the molecule of biological interest to another molecule such as an antibody is evidenced by means of the detecting molecule.

For this purpose, coupling agents must be bifunctional having both a chemical function enabling their coupling with said molecule of biological interest and a further chemical function enabling their coupling with said detecting molecule, and must also have a spacer arm allowing sufficient distancing of the coupled molecules.

Various heterobifunctional coupling agents are known from the prior art. These coupling agents, found in the PIERCE catalogue for example, essentially have a maleimide function, a hydrazone function and a spacer arm of saturated or aromatic alkyl type. These coupling agents are used for coupling molecules having free thiol functions and also for coupling molecules having aldehyde or ketone functions. However, these coupling agents have the disadvantage of being scarcely soluble in aqueous media in particular on account of the hydrophobic nature of the spacer arm, and often require the use of organic co-solvents when used, in particular to prepare conjugates. In addition, the proteins coupled to these coupling agents have a tendency to precipitate during marking.

Mikolajczyk S. et al. (Bioconjugate Chemical, 1994, 5(6), 636–646) describe the use of a coupling agent having a maleimide function, an aminooxyalkylene function and a relatively short spacer arm containing L-lysine in particular. This coupling agent is used for coupling two modified proteins, β-lactamase and the Fab murine peptide fragment. The disadvantages of this coupling agent are that it has a short spacer arm not allowing sufficient distancing of the molecules coupled to the coupling agent, and its synthesis method is long. Also a stability problem of the coupling agent may arise on account of the presence of the lysine —COOH function which could react with the alcoxyamine function known to be highly reactive.

BRIEF SUMMARY OF THE INVENTION

The applicant has now developed novel coupling agents with which to overcome the disadvantages of prior art coupling agents in that they allow sufficient distancing of the coupled molecules, they are highly soluble owing to the nature of their spacer arm and the conjugates obtained are very stable. In addition, the coupling agents of the invention allow improved detection sensitivity for diagnostic tests.

Therefore, a first subject of the present invention consists of coupling agents having the following general formula (I):

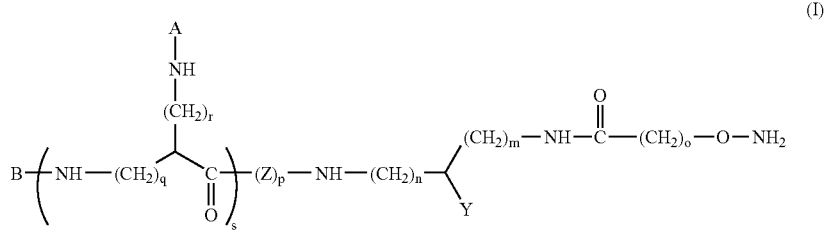

in which:

Z represents —NH—(CH$_2$)$_2$—O—(CH$_2$)$_2$—O—CH$_2$—C(O)—,

A represents a group chosen from among:

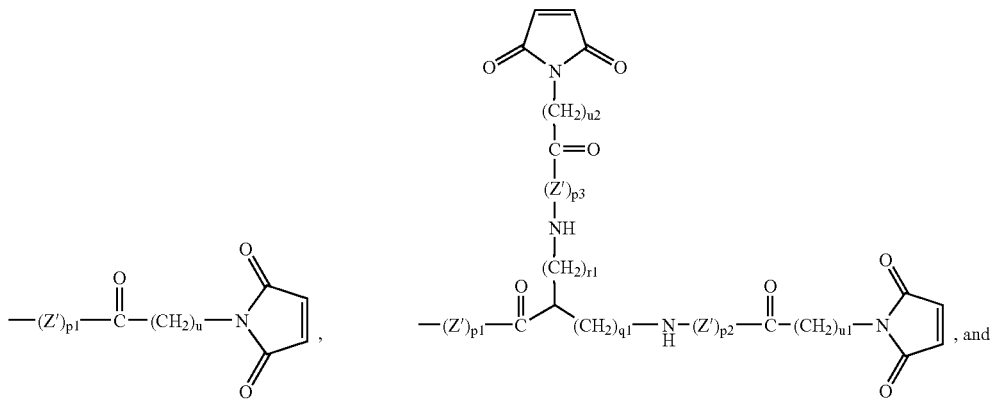

-continued
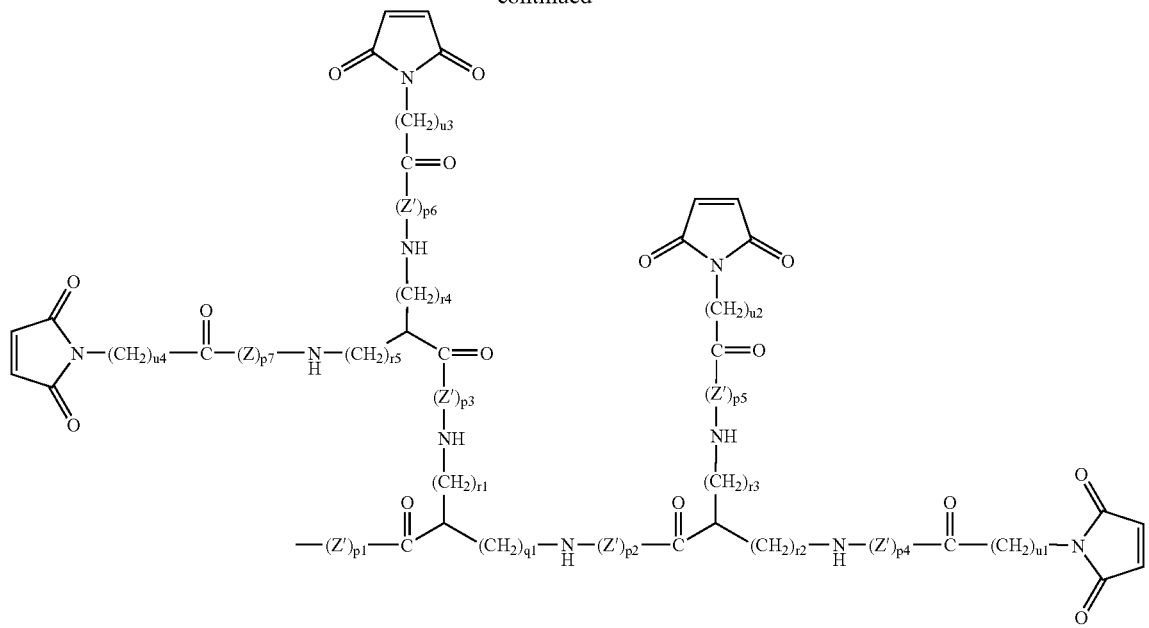
B represents a group chosen from among:
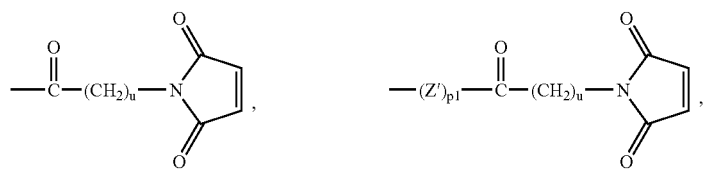
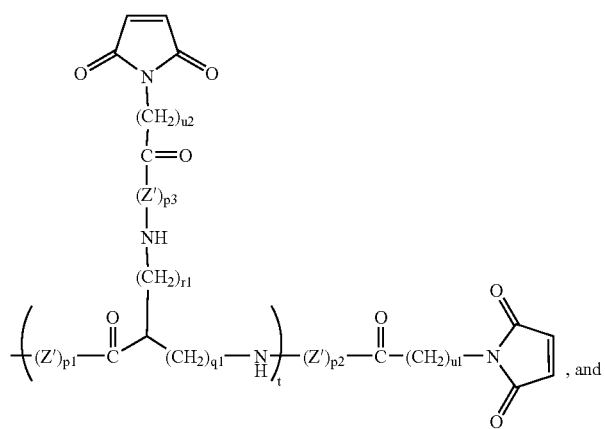
, and

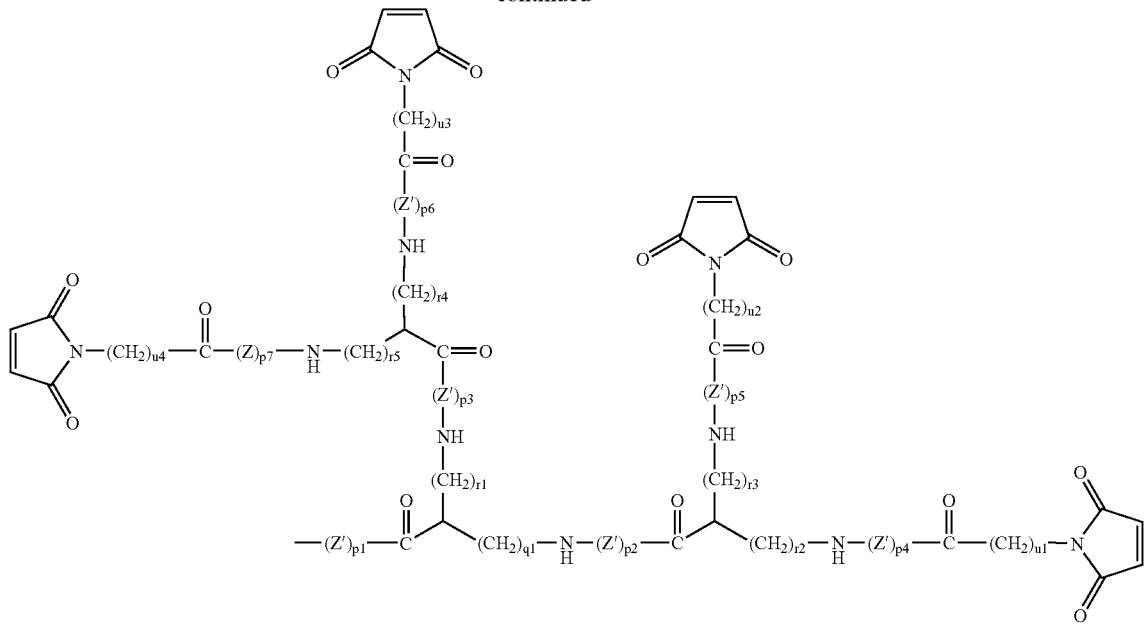

Y represents a group ending with —C(O)—NH$_2$ and which is inert vis-à-vis the aminooxyalkylene function, the maleimide group or groups of B and possibly A and vis-à-vis the pattern —(CH$_2$)$_2$—O—(CH$_2$)$_2$—O—CH$_2$— of Z, Z' represents —C(O)—CH$_2$—O—(CH$_2$)$_2$—O—(CH$_2$)$_2$—NH—, n is an integer lying between 0 and 3,
m is an integer lying between 1 and 3,
o is an integer lying between 1 and 3,
p and p1 to p7 are each independently an integer lying between 1 and 4,
q and q1 are each independently an integer lying between 0 and 3,
r and r1 to r5 are each independently an integer lying between 2 and 5,
s is an integer of 0 or 1,
t is an integer lying between 1 and 7, and
u and u1 to u4 are each independently an integer lying between 2 and 10.

Another subject of the invention consists of activated intermediates formed of a coupling agent such as defined above and of:
 a molecule having on its surface at least one aldehyde and/or ketone function before conjugation, or
 one to eight molecules having on their surface at least one free thiol function before conjugation.

A further subject of the invention consists of conjugates formed of a coupling agent such as defined above and linked firstly to a molecule having on its surface at least one aldehyde and/or ketone function before conjugation, which is preferably a molecule of biological interest, and secondly to one to eight molecules having on their surface at least one free thiol function before conjugation, which are preferably markers.

A final subject of the invention consists of the use of a conjugate such as defined above for in vitro diagnostic methods of diseases involving recognition of a ligand-antiligand pair.

The coupling agents of the invention are as defined in formula (I) above. They are characterized by the presence of:
 an aminooxyalkylene function: NH$_2$—O—(CH$_2$)$_o$—, o being as defined for (I), so that it can specifically bind with a molecule having on its surface at least one aldehyde and/or ketone function,
 one to eight maleimide functions at B and optionally at A to be able to bind specifically with one to eight molecules having on their surface at least one free thiol function, and
 a spacer arm Z of polyethyleneglycol type which is long and is able to impart better solubility to the coupling agent.

Also, the association of the three aforesaid characteristics gives improved stability to the conjugates formed from said coupling agents.

The coupling agents of the invention also contain a Y group that is inert towards the aminooxyalkylene function: NH$_2$—O—(CH$_2$)$_o$—, o being as defined for (I), towards the maleimide group(s) of B and optionally A and towards the —(CH$_2$)$_2$—O—(CH$_2$)$_2$—O—CH$_2$— pattern of Z, i.e. the Y group is unable to react with these patterns or functions. In addition, Y ends in —C(O)—NH$_2$. This —C(O)—NH$_2$ ending is of importance as, unlike the —COOH function such as present in the coupling agent described in Bioconjugate Chemical, 1994, 556, 636–646, it allows the avoidance of any stability problem due to the presence of the aminooxyalkylene. In addition, the coupling agent so obtained does not have any ionic charge. According to a preferred embodiment, Y is —C(O)—NH$_2$.

The coupling agents of the invention may include one to eight maleimide functions allowing the attachment of one to eight molecules having on their surface at least one, generally several, free thiol functions before conjugation, respectively.

It will be noted that «n is an integer between 0 and 3» for example, means that n may be 0, 1, 2 or 3.

In coupling agent (I), each Z or Z' group is linked by its —NH— function to a —C(O)— function and by its —C(O)— function to a —NH— function.

The coupling agents of the invention comprise at least one asymmetric carbon and the different optical isomers form an integral part of the invention. The subject of the present invention is therefore coupling agents of formula (I) in the form of pure isomers but also in the form of a racemic mixture or of any proportion. Coupling agents (I) are isolated in pure isomer form using conventional separation techniques, for example by chiral phase chromatography.

DESCRIPTION OF THE PREFERRED EMBODIMENTS

According to one preferred embodiment, the coupling agents of the invention only have one maleimide function. In this case, s in formula (I) equals 0 and B preferably represents:

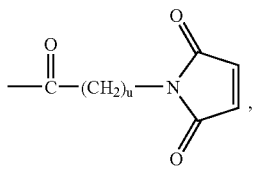

u being as previously defined.

When the coupling agents of the invention have more than one maleimide function, they may either be in dendrimer (or branched) form or in linear form, depending upon the value of A and B.

According to a preferred embodiment, A and B are identical and represent:

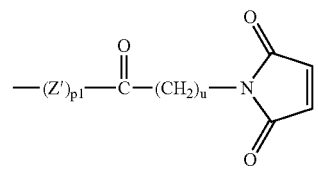

Z', p1 and u being as previously defined,
so that the coupling agents of the invention are in dendrimer form and have two maleimide functions.

According to another preferred embodiment, A and B are identical and represent:

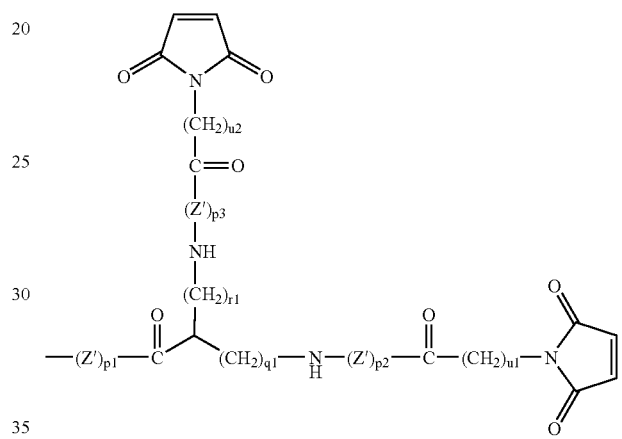

Z', p1, p2, p3, q1, r1, u1 and u2 being as previously defined,
so that the coupling agents of the invention are in dendrimer form and have four maleimide functions.

According to a further embodiment, A and B are identical and represent:

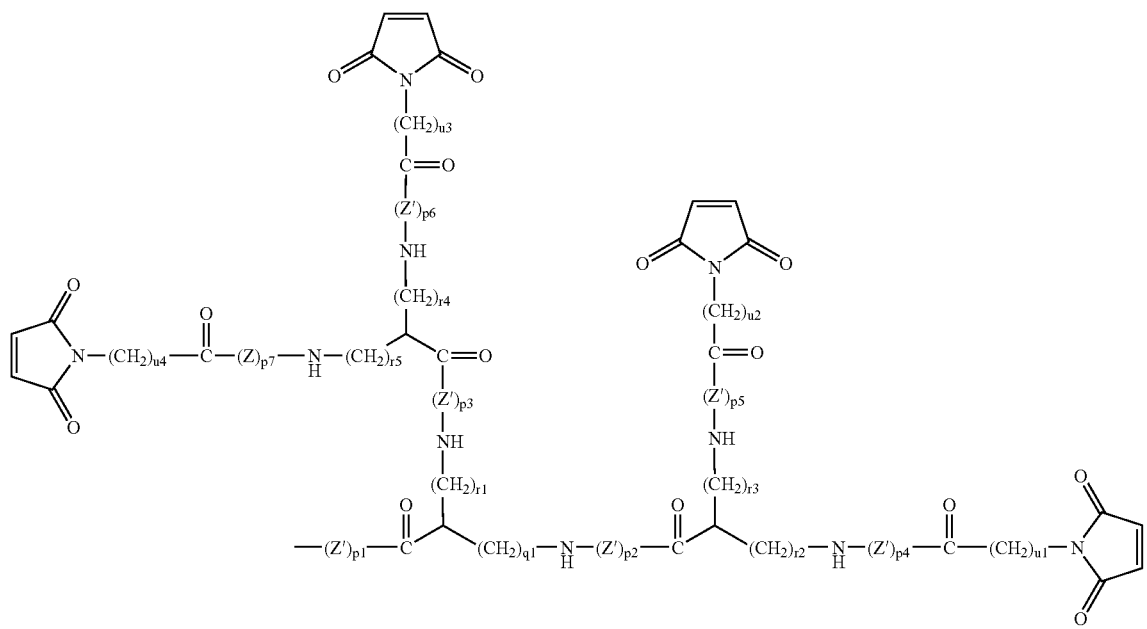

Z, Z', p1 to p7, q1, r1 to r5 and u1 to u4 being as previously defined, so that the coupling agents of the invention are in dendrimer form and have eight maleimide functions.

When the coupling agents are in linear form, A represents:

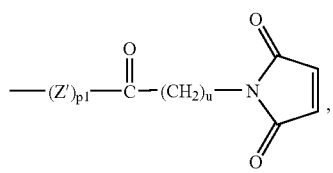

and B represents:

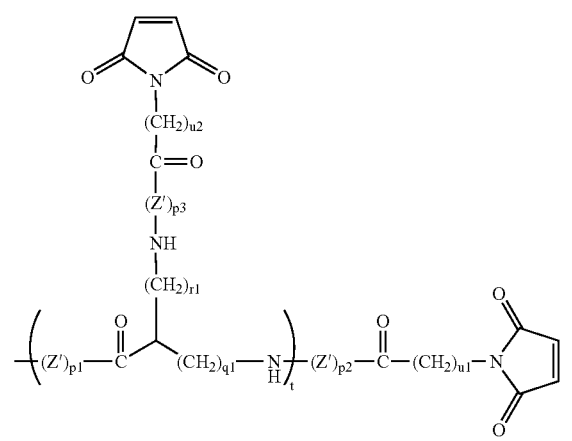

Z', t, p1 to p3, q1, r1 and u, u1 and u2 being as previously defined, and this forms another embodiment of the invention.

In the coupling agents of the invention, the coupling arm may be of varying length, but it must be sufficient to distance the molecules which are to be coupled, in particular on account of their steric hindrance, and when the coupling agents have several maleimide functions which are to be coupled to as many molecules with free thiol functions.

The length of the arms varies in relation to the indices m, n, o, p, p1 to p7, r, r1 to r5, q, q1 and u, u1 to u4.

According to one embodiment, the coupling agents of the invention meet at least one of the following conditions:

n equals 0, m equals 1, p and p1 to p7, when applicable, equal 2, q and q1, when applicable, equal 0, r and r1 to r5, when applicable, equal 4, u and u1 to u4, when applicable, equal 2 and o equals 1.

The preferred coupling agents are chosen from among the following:
compound of formula (I) in which m=1, Y=—C(O)—NH$_2$, O=1, n=0, p=2, s=0 and B represents:

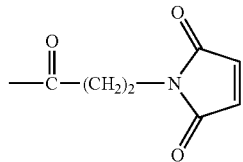

and
compound of formula (I) in which m=1, Y=—C(O)—NH$_2$, o=1, n=0, p=2, r=4, s=1, q=0 and A and B are identical and represent:

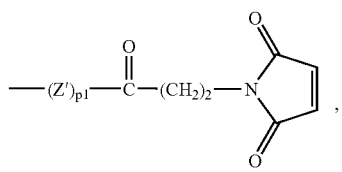

p1 equalling 2.

The coupling agents of the invention are obtained by solid phase synthesis of peptide synthesis type either manually or preferably automatically on commercially available synthesizers such as the ABI 431 A synthesizer. In other words, the coupling agents, which can be divided into the synthons described below, which are amino acid or related synthons, are obtained from a synthesis support (solid phase) such as the commercial resin RINK-Amide-MBHA (NOVABIOCHEM), making possible the attachment of the C-terminal end of the first synthon (synthon I) of the coupling agent to be synthesized before proceeding with the synthesis of said agent by gradually adding suitable synthons chosen from among synthons II to IV:

Synthon I

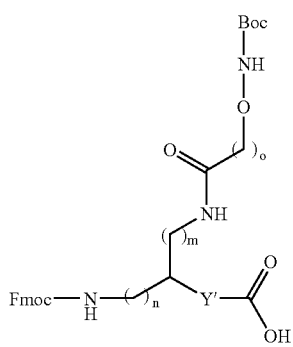

Synthon II

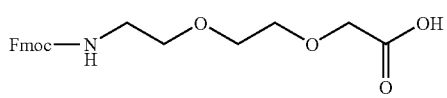

Synthon III

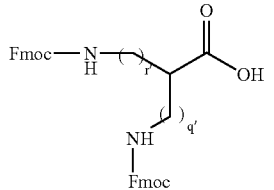

Synthon IV

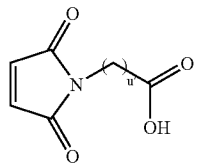

where n, m, and o are as defined previously, q' represents q or q1, r' represents r, r1, r2, r3, r4, or r5 and u' represents u, u1, u2, u3, or u4 such as previously defined, Boc denotes tert-butyloxycarbonyl, Fmoc denotes fluorenylmethoxycarbonyl and Y' corresponds to Y devoid of the —C(O)—NH$_2$ function. The coupling of a synthon IV with a synthon I is made after deprotecting the Fmoc group.

The reagents used during the coupling cycles of the different synthons are known to persons skilled in the art and are described for example in Chemical Approaches to the Synthesis of Peptides & Proteins, Paul Lloyd Williams, Fernando Albericio, Ernest Giralt, CRC Press. After synthesizing the coupling agent of the invention, it is detached from the support following an operating mode known to those skilled in the art (Chemical Approaches to the Synthesis of Peptides & Proteins, supra) and is simultaneously deprotected (Boc group) in the presence of an acidolysis solution such as a solution containing trifluoroacetic acid.

The coupling agents are then purified, for example by semi-preparative BECKMAN HPLC on a C$_{18}$ reverse phase column.

The coupling agents so obtained can be used to couple firstly the molecules having on their surface at least one aldehyde and/or ketone function before conjugation, which will react with the aminooxyalkylene function of the agents, and secondly those molecules having on their surface at least one free thiol function before conjugation which will react with the maleimide function or functions of said agents.

The subject of the invention is therefore activated intermediates formed of a coupling agent of the invention with either a molecule having on its surface at least one aldehyde or ketone function before conjugation, or with one to eight molecules having on their surface at least one free thiol function before conjugation, preferably one to four of said molecules.

According to a preferred embodiment, the activated intermediates are formed of a coupling agent of the invention and of a molecule having on its surface at least one, and generally more than one, aldehyde and/or ketone function before conjugation.

The molecules having aldehyde or ketone functions on their surface comprise all molecules having such functions or which are modified to include such functions. By way of example, peptides having an N-terminal serine or threonine may be cited, and molecules of biological interest such as antigens, antibodies, haptenes, glycoproteins, or any other molecule able to bind with a linkage partner.

The modification of molecules desired to have aldehyde or ketone functions may be performed by reaction with reagents leading to such functions, such as periodate.

As examples of molecules having aldehyde functions, periodate-oxidized glycoproteins may be cited, such as gp160 the envelope glycoprotein of the HIV-1 virus, sugars. As examples of molecules having ketone functions, any molecule may be cited which contains a levulinyl (ketone) group.

According to one preferred embodiment, the molecule having aldehyde functions on its surface is a glycoprotein oxidized with periodate and preferably gp 160 so oxidized.

Persons skilled in the art may easily determine which molecules have free thiol functions on their surface, either naturally or by chemical reaction, before conjugation.

Examples of said molecules comprise markers, which form an embodiment of the invention.

By marker is meant any molecule able to generate a detectable signal either directly or indirectly. A non-limitative list of these markers includes:

enzymes which produce a detectable signal for example by colorimetry, fluorescence, luminescence, such as horseradish peroxidase, alkaline phosphatase, α-galactosidase, glucose-6-phosphate dehydrogenase, chromophores such as fluorescent, luminescent compounds, dyes, radioactive molecules containing $^{32}$P, $^{35}$S or $^{125}$I, and fluorescent molecules, on the understanding that these markers will be optionally modified to have free thiol functions.

According to one embodiment of the invention, the marker is alkaline phosphatase, previously modified.

The modification of molecules desired to have free thiol functions may be conducted by reaction with reagents leading to said functions such as Traut's reagent (Pierce) also called imminothiolane.

With alkaline phosphatase, modification is performed in the presence of TRAUT's reagent (Pierce).

The quantity of marker to be used depends upon the number of maleimide functions contained in the coupling agent of the invention that is used. It may easily be determined by persons skilled in the art.

Evidently, the aforesaid examples, firstly in respect of molecules having at least one aldehyde and/or ketone function, and secondly of molecules having at least one free thiol function, are not restrictive and are interchangeable. In other words, for example, a coupling agent may be coupled, via its maleimide function, with a molecule of biological interest modified to include at least one free thiol function, and, via its aminooxyalkylene function, with a marker modified to include at least one aldehyde and/or ketone function.

Both types of molecules having the functions described above linked to coupling agents of the invention form conjugates which constitute a further subject of the invention.

According to an embodiment of the invention, the conjugates of the invention meet at least one of the following conditions:

the molecule having at least one aldehyde and/or ketone function is a molecule of biological interest, in particular previously oxidized glycoprotein gp 160, and the molecule or molecules having at least one free thiol function are markers, in particular previously modified alkaline phosphatase.

The conjugates so obtained may be used for in vitro diagnosis methods of diseases involving recognition of a ligand/anti-ligand pair, the molecule of biological interest forming the ligand.

With the conjugates of the invention it is possible for example to determine in a biological sample the presence of an anti-ligand which will attach itself to the ligand of said conjugate, such attachment being detected by means of the marker of said conjugate.

Examples of ligand/anti-ligand pairs are well known to persons skilled in the art, which is the case for example for the following pairs: biotine/streptavidine, haptene/antibody, antigen/antibody, peptide/antibody, sugar/lectine, polynucleotide/complementary polynucleotide, one of the elements of these pairs evidently forming the molecule of biological interest.

The in vitro diagnosis methods able to use the conjugates of the invention are sandwich type methods in particular which are largely known to persons skilled in the art. As an example the ELISA method may be cited, or the ELOSA method, ELISPOT method and Western-blot method.

Those diseases which may be diagnosed with the complexes of the invention are unlimited and include all diseases detected by the presence of a specific marker of the disease, of the type molecule of biological interest, for which a linkage partner exists. As an example, viral diseases such as AIDS may be cited, and solid cancers such as breast or prostate cancer.

The coupling agents of the invention, such as defined previously, are able to improve the in vitro diagnosis of diseases by using direct coupling of a molecule of biological interest with one or more markers, with no intermediate biotinylation of said molecule of interest, owing to the length of their spacer arms and good stability of the formed conjugates. In addition, the use of the coupling agents of the invention makes it possible to amplify the detection of the ligand/anti-ligand bond since said coupling agents may bind with up to eight markers while solving the steric hindrance problem of a large number of molecules.

The invention will be more readily understood with the assistance of appended FIG. 1, which shows the enzymatic tracing using a conjugate of the invention, and with the assistance of the following examples which are given as non-restrictive examples.

EXAMPLES

Example 1

Compound of formula (I) in which m=1, Y=—C(O)—NH$_2$, o=1, n=0, p=2, s=0 and B represents:

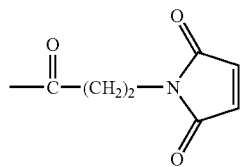

282 μmoles of Fmoc-RINK-Amide-MBHA resin (Novabiochem) were placed in the reactor of a 431 A automatic synthesizer (Applied Biosystems). Four cartridges of the three synthons I, II and IV were prepared containing ⅓ mmole of each synthon as follows:

one cartridge containing 166.4 mg (approx. 333 μmol) of the following synthon (corresponding to synthon I):

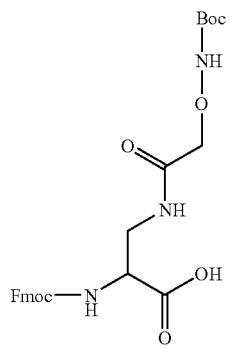

where Boc denotes t-butyloxycarbonyl and Fmoc denotes fluorenylmethoxycarbonyl, two cartridges each containing 128.5 mg (approx. 333 μmol) of synthon II:

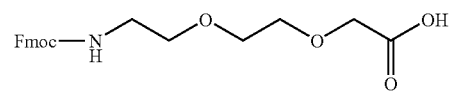

in which Fmoc is as defined above, and:

one cartridge containing 56.4 mg (approx. 333 μmol) of synthon IV:

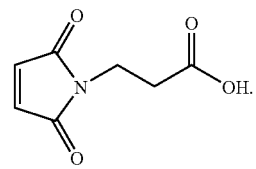

The following coupling cycle was conducted four times with the aforesaid cartridges, in the following order:

rinsing and et solvation of the resin with N-methylpyrrolidinone (NMP), dual treatment, for approximately 4 min, then for more than 10 min, of synthon I (1$^{st}$ passage) or of the synthon(s)/resin complex (3$^{rd}$ to 4$^{th}$ passage) with a solution of piperidine of approximately 40% in NMP to deprotect the Fmoc group, simultaneously, dilution in a minimum amount of NMP and preactivation of the synthon in its cartridge through the addition of one equivalent of the coupling agent hexafluorophosphatebenzotriazolyltetramethyluronium (HBTU) in the form of a 0.2 M HBTU solution in N,N-dimethylformamide, emptying the reactor and multiple rinsing of the resin with NMP, transfer of the content of the synthon cartridge to the reactor and addition to the reactor of approx. 2.5 equivalents of the tertiary coupling base disopropylethylamine (DIEA) in the form of a 1.67 M DIEA solution in NMP, and coupling for one hour and reactor emptying.

Subsequently, a resin rinsing cycle was performed with several rinsings in NMP, followed by dichloromethane (DCM).

Deprotection and detaching of the coupling agent was then conducted by leaving it to react at room temperature for one hour in approximately 6.5 ml of trifluoroacetic acid solution (TFA) with 5% water, then by transferring the liquid phase into a container containing approximately 100 ml ethyl ether at −10° C. and rinsing the resin with approximately 4 ml TFA and 4 ml DCM, these latter liquid phases having been added to the first in the ether container.

The container containing the coupling agent was centrifuged at 3500 rpm at −5° C. for 10 min and the ethereal supernatant was removed. This operation was repeated twice after addition of ether.

After vacuum drying, 0.14 g of crude mixture was obtained.

The presence of the coupling agent was verified in the crude mixture by taking up the mixture in MilliQ demineralized water (Waters System) and by analysing an aliquot quantity of this mixture by BECKMANN HPLC (reverse phase $C_{18}$ VYDAC chromatography column, eluant $E_A$ solution of MilliQ demineralized water with 0.1% TFA, eluant $E_B$ solution of 95% acetonitrile and 5% MilliQ water with 0.1% TFA, purification rate 1 ml/min) using a gradient of 0 to 80% acetonitrile over 30 minutes. Under these conditions, the coupling agent has a retention time in the order of 9.7 min (dead volume peak at around 3 min).

The coupling agent was purified with semi-preparative BECKMAN HPLC (reverse phase $C_{18}$ VYDAC chromatography column, eluant $E_A$ solution MilliQ demineralized water with 0.1% TFA, eluant $E_B$ solution of 95% acetonitrile and 5% MilliQ water with 0.1% TFA, purification rate 22 ml/min). The programmed gradient for this purification was as follows:

0% eluant $E_B$ from t=0 to 10 min,
change to 5% eluant $E_B$ from t=10 to 11 min and
change to 19% eluant $E_B$ from t=11 to 41 min.

Fractions were taken as from t=16.5 min at the rate of 0.2 min per tube and for 40 tubes. Isocratic analysis was made of tubes 11 to 40 for 10 min with 11% eluant $E_B$ on the analytical system.

The purest fractions were grouped together and freeze-dried in a VIRTIS freeze-drier. After freeze-drying and weighing, the product was taken up in MilliQ water and aliquoted in an Eppendorf tube.

Example 2

Compound of formula (I) in which: m=1, Y=—C(O)—NH$_2$, o=1, n=0, p=2, r=4, s=1, q=0 and A and B are identical and represent:

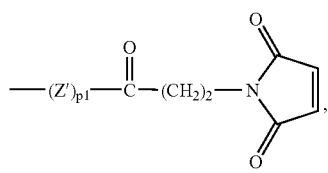

p1 equalling 2

To prepare the title compound, the operating mode described in example 1 was repeated, with the sole exception that the starting product was 153 μmol of reaction product between the resin, a cartridge of synthon I and two cartridges of synthon II such as described in example 1, and the following synthon cartridges were used:

one cartridge containing approximately 166 μmol of the following synthon (corresponding to synthon III:

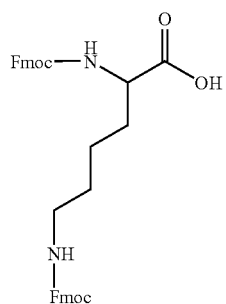

in which Fmoc is such as defined above, four cartridges each containing approximately 333 μmol of synthon II:

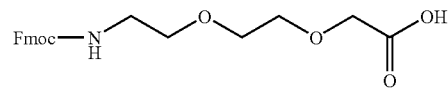

in which Fmoc is such as defined above, and
two cartridges containing approximately 333 μmol of the following synthon IV:

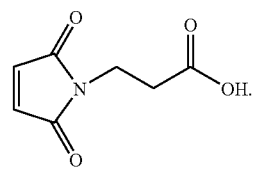

In this manner a product in gum form was obtained which was purified as indicated above except that the following gradient cycle was used:

10% eluant $E_B$ from t=0 to 10 min,
change to 15% eluant $E_B$ from t=10 to 11 min, and
change to 27% eluant $E_B$ from t=11 to 41 min.

Example 3

Preparation of the Activated Intermediate gp 160/Coupling Agent of the Invention The glycoprotein gp160 (ABL) was dialysed overnight at 2–8° C. against a 50 mM acetate buffer pH 4.5 in the presence of 0.01% SDS. The glycoprotein obtained was oxidized with 5 mM NaIO$_4$ in darkness for 15 min at 18–25° C. The reaction was blocked with ethyleneglycol (1/200) and the oxidized protein was dialysed against a 25 mM solution of sodium tetraborate pH 5.5.

A solution of the coupling agent was prepared as in example 2 with 2 mg/ml in a sodium tetraborate solution.

The coupling agent solution was mixed with the oxidized glycoprotein to the proportion of 20 mol coupling agent per 160 000 Da unit of glycoprotein and was incubated for one hour at 18–25° C. under stirring to achieve coupling.

The mixture obtained was dialysed against a 50 mM phosphate buffer, 150 mM NaCl, at pH 6.8.

Example 4

Preparation of the Conjugate gp160/Coupling Agent/Alkaline Phosphatase

The alkaline phosphatase was modified to include free thiol groups as follows: the alkaline phosphatase (Biozyme) was dialysed against 10 mM phosphate buffer, 5 mM EDTA at pH 8. A solution of Traut's reagent (Pierce) was prepared with 3 mg/ml in 10 mM phosphate buffer, 5 mM EDTA, at pH 8 and left to incubate 2 hours at 18–25° C. The reaction mixture was desalted on a Sephadex G-25 column (Pharmacia).

1 mg of activated intermediate obtained in example 3 was mixed with 3 mg modified alkaline phosphatase and left to incubate overnight at 2–8° C. under stirring. The reaction was blocked (maleimide groups) through the addition of a 10 mM β-mercaptoethanol solution to the buffer at pH 6.8 and left to incubate 15 min at room temperature. The reaction was blocked (residual thiol functions) with a solution of N-ethylmaleimide (Sigma) in the buffer at pH 6.8 and left to incubate 15 min at room temperature. Dialysis was then conducted for twice 45 min at room temperature and overnight at 2–8° C. against the PBS buffer.

The conjugate was then purified on the Superdex 200 chromatography column (Pharmacia) (eluant: PBS, azide with 0.01% SDS, flow rate: 1 ml/min, fractions: 1 ml).

The enzymatic activity of the chromatography fractions was examined using a microplate test consisting of sampling 25 μl of each fraction, making up to 100 μl with PBS, adding 100 μl pNPP, leaving to incubate for 5 min, blocking the reaction with 20 μl 0.5 N NaOH and measuring the optical density.

The tracing of the enzymatic activity of this test is given in the single FIGURE which evidences the good marking level obtained. The different fractions are indicated over the abscissa axis.

The optical densities of the conjugate alone at 280 nm (curve 1), and of the conjugate after enzymatic reaction at 405 nm (curve 2), were measured.

Example 5

Comparison of the Detection Sensitivity of a Conjugate of the Invention and of a Conjugate Obtained with a Pierce Coupling Agent A conjugate obtained with the coupling agent of example 1 was used and a conjugate obtained with the Pierce coupling agent (EMCH, such as described below) and the sensitivity was compared in terms of detection achieved by these different conjugates.

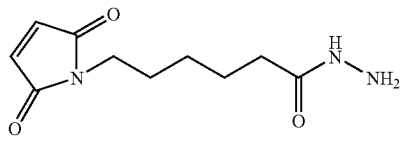

EMCH (MW 225.24)

For this purpose, in a reaction tank 150 μl of 1 μm magnetic particles were added in a 1% suspension and diluted to ⅕oin a buffer (200 mM Tris—150 mM NaCl pH 8.5—BSA 10 g/l —5% Tween 20, NaN₃ 0.9 g/l), functionalised with —COOH groups and sensitized with the gp160 glycoprotein of the HIV-1 virus, and 150 μl of sample. The tested samples were either a pool of negative HIV-1 (HIV-1−) sera, or samples containing the HIV-1 (HIV-1+) virus diluted in a pool of negative sera. They were left to incubate 15 min at 37° C.

Subsequently 150 μl of reagent were added containing the conjugates gp160/coupling agent/alkaline phosphatase prepared following the operating mode described in example 4 using the appropriate coupling agent and diluted to an approximate concentration of 2 μg/ml in a buffer of 100 mM Tris—300 mM NaCl pH 7.4—Mannitol 2.5 g/l—NaN₃ 0.9 g/l—Régilait® milk 2.5 g/l—BSA 2.5 g/l—0.1 mM ZnCl₂—1 mM MgCl₂. This was left to incubate 15 min at 37° C.

Three washings were conducted with a washing solution formed of a citrate buffer pH 6 containing NaCl, a detergent, an anti-foaming agent and anti-microbial agent (MAGIA, Biotrol).

The luminescence substrate Lumiphos 530 (Lumigen) was added to the reaction tank and left to incubate for 15 min at 37° C.

Luminescence was read off in RLU units (Relative Luminescence Unit) using a H7155 photomultiplier (HAMAMATSU) and the luminescence ratio was calculated between the samples containing the virus and those without the virus.

The results are given in table 1 below.

TABLE 1

Sensitivity test

| | Luminescence RLU | | | | |
|---|---|---|---|---|---|
| Conjugate | HIV-1 − a1 | HIV-1 + (1/2000) a2 | HIV-1 + (1/300) a3 | Ratio a2/a1 | Ratio a3/a1 |
| with example 1 | 1170 | 58342 | 3409 | 49.9 | 2.9 |
| with EMCH | 8103 | 134104 | 10621 | 16.6 | 1.3 |
| with EMCH (factor 2dilution) | 3731 | 61526 | 5033 | 16.5 | 1.35 |

The ratios obtained with the conjugate of the invention and with a conjugate prepared with EMCH such as indicated above, clearly show the improvement in detection sensitivity when a coupling agent of the invention is used, whether or not dilution is extensive (last 2 columns in the table).

It is to be noted that, to obtain a control detection level (background noise) comparable with the level obtained with the conjugate of the invention, the conjugate prepared from EMCH was diluted by a factor of 2 (last line). It was therefore possible to verify that, with comparable background noise, the luminescence ratio remains low for the conjugate prepared from the coupling agent of the prior art.

Example 6

Comparison of Stability Between a Conjugate of the Invention and a Conjugate Obtained with the EMCH Coupling Agent To study the stability of the conjugates, the diluted conjugates were left to age as indicated in example 5, in an oven at 37° C. 8, 15 and 30 days and their behaviour was compared with the same preparations stored at 4° C. The percentage results are given in table 2 below.

TABLE 2

Stability test

| | 8 days at + 37° C. | 15 days at + 37° C. | 30 days at + 37° C. |
|---|---|---|---|
| Conjugate of the invention | −8.7% | −13.2% | −37.1% |
| Conjugate with EMCH | −36.7% | −57.3% | −56.8% |

The results of table 2 clearly show that under forced aging conditions, the conjugate prepared with the coupling agent of the invention is much more stable than the conjugate prepared with a coupling agent of the prior art.

Example 7

Preparation of the Coupling Agent Described by Mikolajczvk S. et al. (supra)

All preparative operations were conducted on a 431 A automatic peptide synthesizer (APPLIED BIOSYSTEMS) at room temperature, in accordance with the following schema:

Approximately 0.68 mole (in chloride equivalent) of highly acid labile 2-chlorotrityl chloride resin (Novabiotech) were placed in the reactor.

Using a semi-automatic protocol, this resin was functionalised through the addition of a solution containing 1 mmole (approx. 535 mg) Fmoc-Lys(Dde)-OH (Dde: (4,4-dimethyl-2,6-dioxocyclohex-1-ylidene)ethyl, NOVABIOCHEM) and 1 mmole diisopropylethylamine (DIEA, ALD-

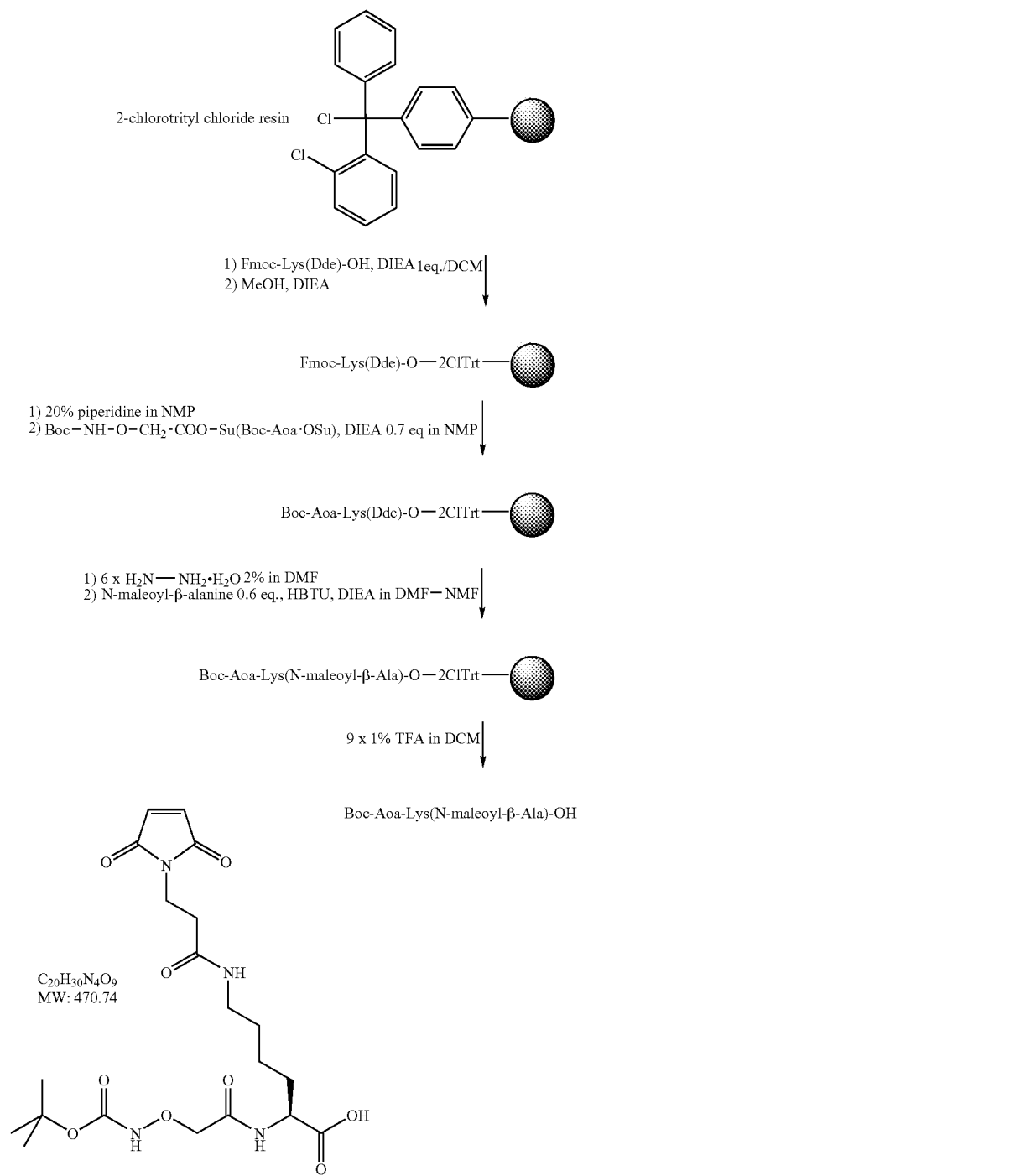

RICH) in 6 ml dichloromethane (DCM, ABI) to fix the lysine protected on the resin by a chemical bond of ester type.

After vortexing for 35 minutes, 0.5 ml anhydrous methanol (MERCK) were injected into the reactor with 5 ml of a 5M solution of 2.5 mmoles DIEA in N-methylpyrrolidone (NMP, ABI).

After washing the resin several times with DCM, a 20–30% piperidine solution (ALDRICH) was caused to react under stirring in NMP for 2 times 5 minutes. The resin was then rinsed several times with NMP and DCM.

A solution was placed on the resin containing 6 ml DCM and approximately 0.69 mmole Boc-Aoa-Osu and 0.25 ml of the 5M solution of 1.25 mmole DIEA in NMP already described above. The coupling reaction lasted 55 minutes under stirring. The resin was then rinsed several times with NMP.

To perform selective deprotection of the Dde group, the resin was treated 6 times 3 minutes with 8 ml of a 2% solution of hydrazine hydrate (ALDRICH) in dimethylformamide (DMF ALDRICH). Several rinsings were then conducted with NMP.

To couple N-maleoyl-β-alanine, 0.6 mmole of N-maleoyl-β-alanine (FLUKA), i.e. approx. 100 mg taken up in approx. 5 ml NMP, were left to react on the resin with 1 ml of a 0.6M solution of 1 equivalent HBTU coupling agent (QUANTUM APPLIGENE) in the DMF and 300 µl of 5M DIEA solution of 2.5 equivalents of DIEA in the NMP. Coupling under stirring lasted around 40 minutes, after which the resin was rinsed several times with NMP and then with DCM.

The coupling agent was detached from the resin by mild acidolysis on the resin treated at room temperature 9 times 2 minutes with 5.5 ml of a 1% solution of trifluroacetic acid (TFA, ACROS) in DCM. Each of these volumes was collected and they were added to 80 ml diethyl ether (SDS) previously cooled to −10° C. The ethereal mixture was evaporated in a rotary evaporator (BÜCHI type) in fractions of a few dozen ml added to a volume of 50 ml cyclohexane (PROLABO) to remove the ether, the DCM, TFA and cyclohexane. Product recovery was 0.14 g, which represents a gross yield of 44%.

The coupling agent was purified and analyzed as follows:

All the product so obtained was slowly taken up in 2 ml acetonitrile (ACN, MERCK). When solubilisation was complete, 1 ml demineralized water was added and the solution transferred to a sampling bottle. The flask was rinsed with a mixture of 2 ml ethanol and 1 ml water which were added to the first collection volume (3 ml). This operation was repeated with water to finally obtain the coupling agent in approximately 50 ml of clear mixture containing 4% ACN and 4% ethanol. This volume was injected in several injections into a BECKMAN semi-preparative high performance liquid chromatography column (fitted with model 126 pumps and 166 UV detector), with VYDAC reverse phase $C_{18}$ column (reference 218TP152022) at a flow rate of 22 ml.min$^{-1}$. The working wavelength was 214 nm. The 2 eluants used for this purification were A) «milliQ»demineralized water (WATERS) with 0.1% TFA and B) a 95% ACN—5% water mixture with 0.1% TFA.

The column was maintained at 10% of B) for 10 minutes to allow the injection of the solution to be purified, then increased to 20% of B) over 1 minute thereafter continuing with a flat gradient of 20 to 31% B) over 30 minutes. At the column outlet 12 fractions were collected as from 19.3 minutes at the rate of 0.25 minute per tube.

An aliquot of each fraction was analyzed by BECKMAN analytical HPLC with the same eluants as previously, but on a smaller reverse phase $C_{18}$ VYDAC column (reference 218TP54), with a flow rate of 1 ml.min$^{-1}$ and a constant (isocratic) proportion of eluant B) of 26% over 10 minutes. The fractions found to be the purest were grouped together and freeze-dried to obtain 12.6 mg of product, i.e. an apparent yield before final assay of the coupling agent of 2.7% since the start of synthesis. The coupling agent was taken up in a 50% ACN aqueous solution and aliquoted into fractions of 580 µg each (500 µg theoretical of which it was verified that these fractions were 580 µg), which were freeze-dried. The structure of the protected coupling agent was confirmed by PE-SCIEX mass spectrometry (API100 model) in which M=470.4 daltons (average theoretical 470.48 and mono-isotopic 470.20).

The coupling agent was deprotected by causing one of the 580 µg aliquots to react with 100 µl TFA under stirring for 30 minutes at room temperature. This solution was then transferred to a 2 ml glass recipient adapted to the centrifuger and to which 3 rinsings of 100 µl DCM were added. Evaporation was performed in a SPEED VAC® vacuum centrifuger for 15 minutes. This yielded 580 µg coupling agent, i.e. a yield of 4.6%.

Example 8

Comparison of the Detection Sensitivity of a Conjugate of the Invention and a Conjugate Obtained with the Coupling Agent Obtained in Example 7

Conjugates of gp 160/coupling agent/alkaline phosphatase were prepared f allowing the operating mode indicated in examples 3 and 4, with the coupling agent of the invention described in example 1 and with the coupling agent of Mikolajczyk S. et al. such as described in example 7, with the exception that for the prior art coupling agent:

i) compared with example 7 deprotection was conducted as follows: a freeze-dried aliquot of the coupling agent (580 µg) was taken and left to react with 100 µl trifluoroacetic acid for 30 minutes at room temperature and under stirring. This reaction mixture was then transferred to a flask compatible with the «SPEED VAC»vacuum centrifuger and to which were added the 2 dichloromethane rinsing products (2×100 µl). Drying was conducted for 20 minutes on this apparatus (without heating the chamber) to obtain a slightly yellow residue of said coupling agent, ii) for the oxidation step of gp160 (example 3), a 0.2 M solution of $NaIO_4$ was used and it was blocked with a ¹/₁₅₀ solution of ethyleneglycol.

To determine detection sensitivity, the operating mode described in example 5 was used, with the exception that 250 µl of magnetic particles were used and a conjugate solution concentration of 0.5 µg.ml$^{-1}$, as well as sera with a scarcely positive HIV-1 content (HIV-1+low), fairly positive HIV-1 content (VIH-1+average) and highly positive HIV-1 content (VIH-1+high).

By scarcely positive sera is meant sera scarcely rich in anti-HIV antibodies, i.e. whose detection measurement is close to threshold when analysed with a commercial kit. By fairly positive sera is meant sera fairly rich in antibodies and by highly positive sera is meant sera highly rich in antibodies.

Luminescence in RLU units and the luminescence ratios obtained with the two compounds are given in table 3 below.

TABLE 3

| | Luminescence RLU | | | | | | |
|---|---|---|---|---|---|---|---|
| Conjugate | HIV-1 − a1 | HIV-1 + low a2 | VIH-1 + average a3 | VIH-1 + high a4 | Ratio a2/a1 | Ratio a3/a1 | Ratio a4/a1 |
| with example 1 | 1291 | 18258 | 99444 | 655177 | 14.14 | 77.01 | 507.36 |
| with example 7 | 2386 | 15688 | 90593 | 517137 | 6.57 | 37.97 | 216.74 |

Here again, the ratios obtained with the conjugate of the invention and with a conjugate prepared with the coupling agent of Mikolajczyk S. et al. such as indicated above, clearly show the improvement in detection sensitivity when the coupling agent of the invention is used.

The invention claimed is:

1. Coupling agent having the following general formula:

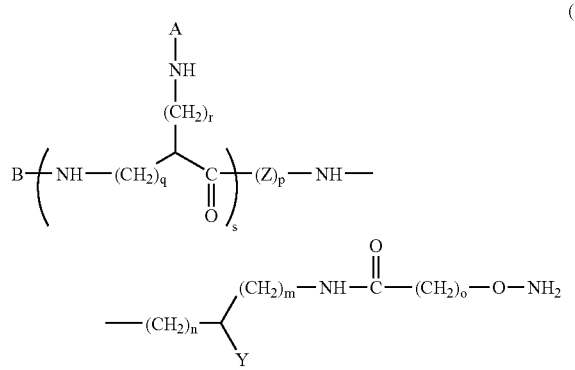

(I)

in which:
Z represents —NH—$(CH_2)_2$—O—$(CH_2)_2$—O—$CH_2$—C(O)—
A represents a group chosen from among:

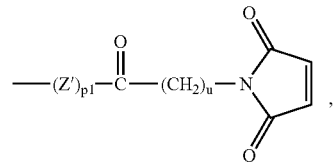

,

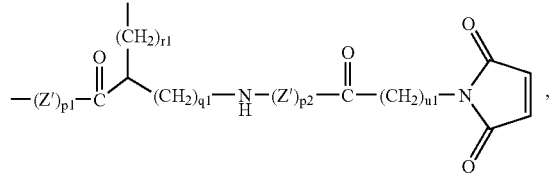

,

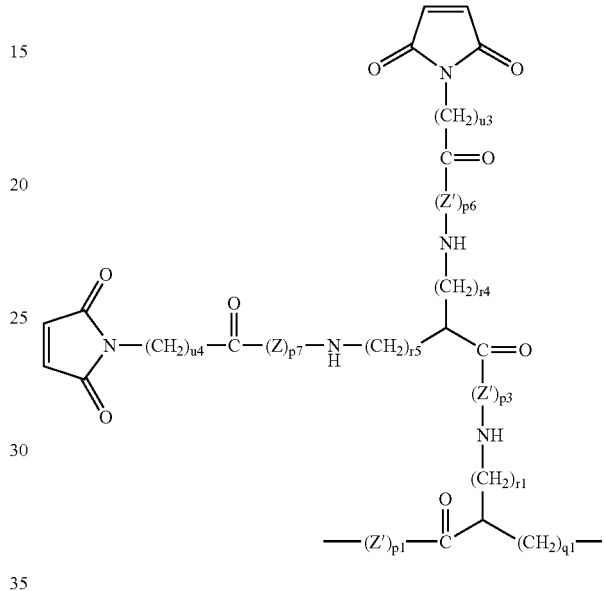

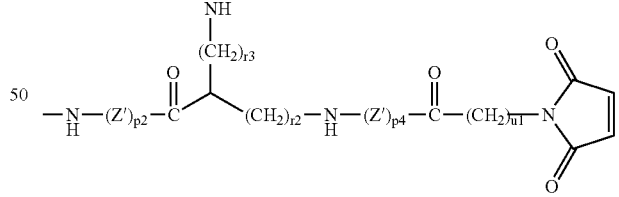

B represents a group chosen from among:

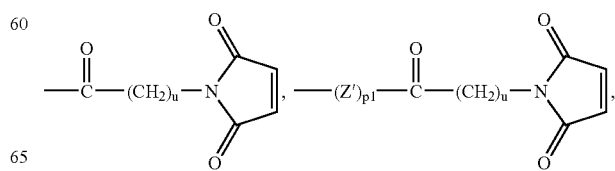

-continued

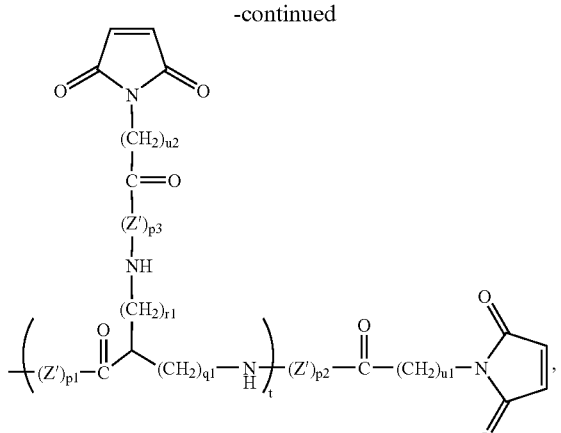

and

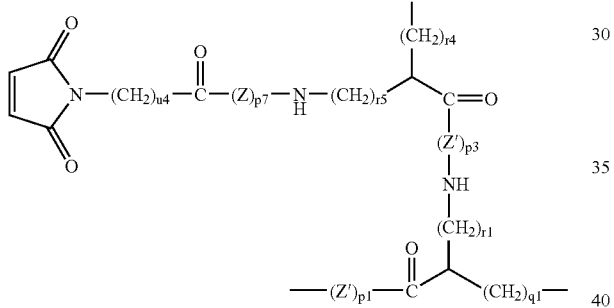

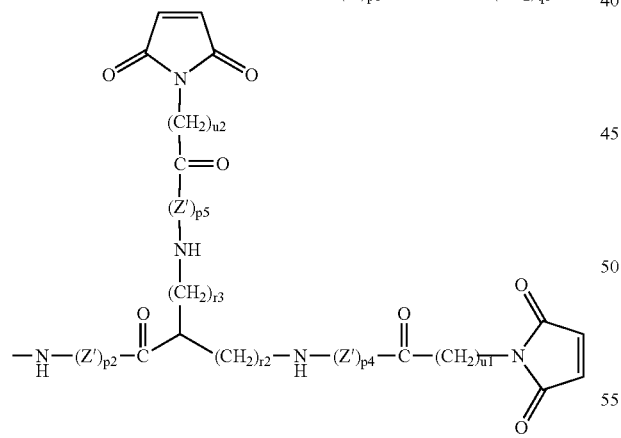

wherein B or B and A are present,

Y represents a group ending in —C(O)—NH$_2$ and which is inert with respect to the aminooxyalkylene function, the maleimide group or groups of B and A and which is inert with respect to —(CH$_2$)$_2$—O—(CH$_2$)$_2$—O—CH$_2$— of Z, Z' represents —C(O)—CH$_2$—O—(CH$_2$)$_2$—O—(CH$_2$)$_2$—NH—, n is an integer lying between 0 and 3, m is an integer lying between 1 and 3, o is an integer lying between 1 and 3, p and p1 to p7 are each independently an integer lying between 1 and 4, q and q1 are each independently an integer lying between 0 and 3, r and r1 to r5 are each independently an integer lying between 2 and 5, s is an integer of 0 or 1, t is an integer lying between 1 and 7, and u and u1 to u4 are each independently an integer lying between 2 and 10.

2. Coupling agent as in claim 1, characterized in that Y is —(C(O)—NH$_2$.

3. Coupling agent as in claim 1, characterized in that s equals 0.

4. Coupling agent as in claim 3, characterized in that B represents:

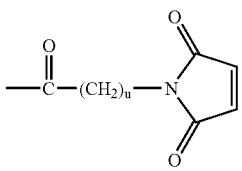

u being such as defined in claim 1.

5. Coupling agent as in claim 1, characterized in that A and B represent:

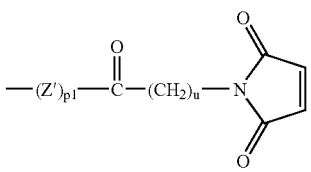

Z', p1 and u being such as defined in claim 1.

6. Coupling agent as in claim 1, characterized in that A and B represent:

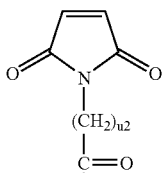

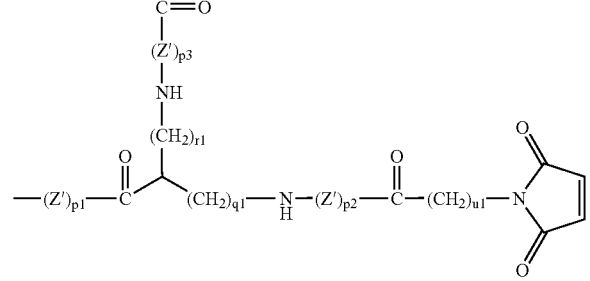

Z', p1, p2, p3, q1, r1, u1 and u2 being such as defined in claim 1.

7. Coupling agent as in claim 1, characterized in that A and B represent:

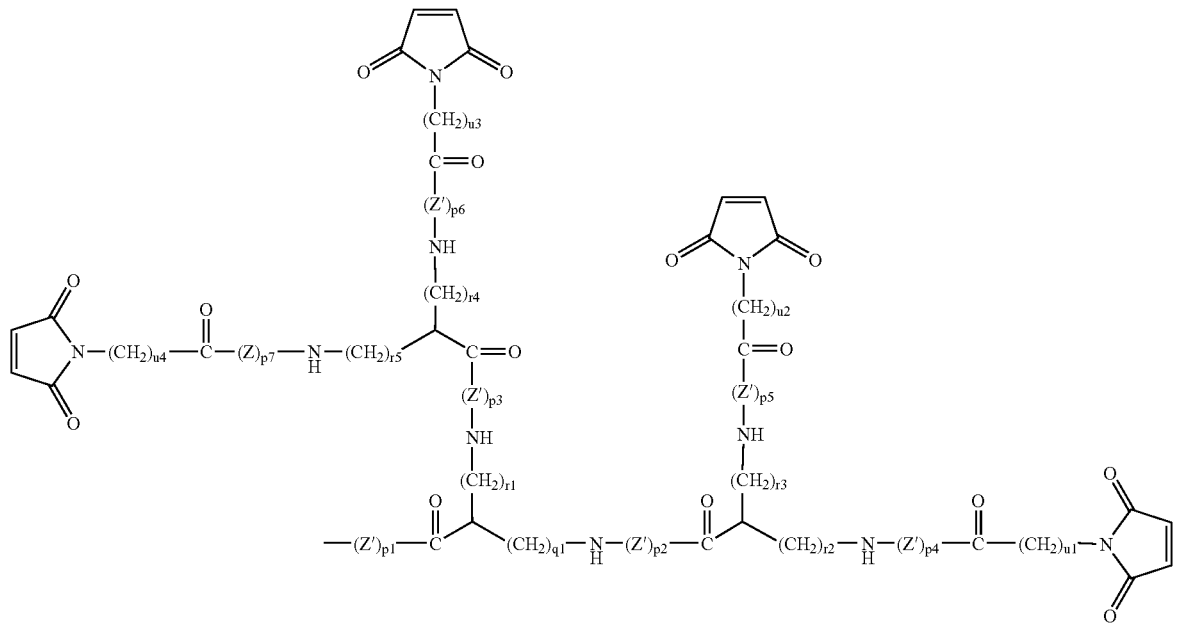

Z, Z', p1 to p7, q1, r1 to r5 and u1 to u4 being such as defined in claim 1.

8. Coupling agent as in claim 1, characterized in that A represents:

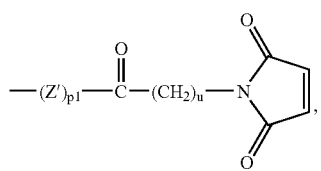

and
B represents:

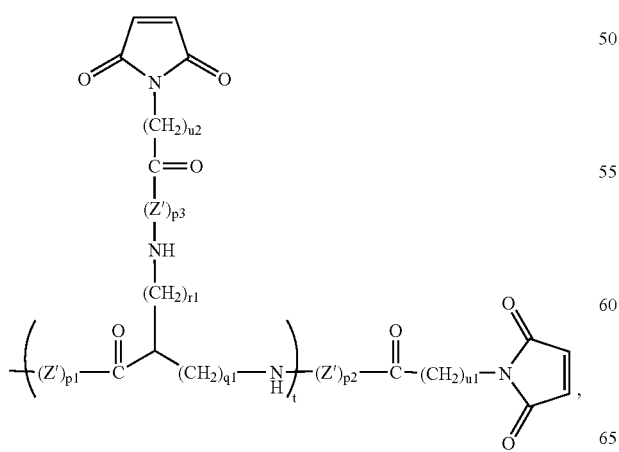

Z', t, p1 to p3, q1, r1, u, u1 and u2 being such as defined in claim 1.

9. Coupling agent as in claim 1, characterized in that n equals 0.

10. Coupling agent as in claim 1, characterized in that m equals 1.

11. Coupling agent as in claim 1, characterized in that p and p1 to p7, when applicable, equal 2.

12. Coupling agent as in claim 1, characterized in that q and q1, when applicable, equal 0.

13. Coupling agent as in claim 1, characterized in that r and r1 to r5, when applicable, equal 4.

14. Coupling agent as in claim 1, characterized in that u and u1 to u4, when applicable, equal 2.

15. Coupling agent as in claim 1, characterized in that o equals 1.

16. Coupling agent as in claim 1, characterized in that it is:

the compound of formula (I) in which m=1, Y=—(C(O)—NH$_2$, o=1, n=0, p=2, s=0 and B represents:

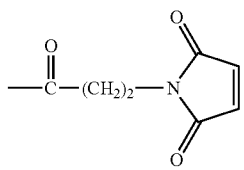

or the compound of formula (I) in which m=1, Y=—(C(O)—NH$_2$, o=1, n=0, p=2, r=4, s=1, q=0 and A and B are identical and represent:

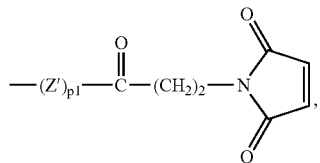

p1 equalling 2.

17. Activated intermediate formed of a coupling agent as in claim 1 and of a molecule having at least one aldehyde and/or ketone function before conjugation.

18. Activated intermediate as in claim 17, characterized in that the molecule having at least one aldehyde function is a glycoprotein oxidized with periodate.

19. Activated intermediate as in claim 18, characterized in that said glycoprotein is the gp160 glycoprotein.

20. Activated intermediate consisting of a coupling agent as in claim 1 and of one to eight molecules having at least one free thiol function before conjugation.

21. Activated intermediate as in claim 20, characterized in that it contains from one to four molecules having at least one free thiol function before conjugation.

22. Activated intermediate as in claim 20, characterized in that said molecule(s) having at least one free thiol function is(are) a marker.

23. Activated intermediate as in claim 22, characterized in that the marker is alkaline phosphatase previously modified to include free thiol functions.

24. Conjugate formed of a coupling agent as in claim 1 linked to a molecule having at least one aldehyde and/or ketone function before conjugation, and to one to eight molecules having at least one free thiol function before conjugation.

25. Conjugate as in claim 24, characterized in that the molecule having at least one aldehyde and/or ketone function before conjugation is a molecule of biological interest.

26. Conjugate as in claim 25, characterized in that the molecule of interest is the gp160 glycoprotein previously oxidized.

27. Conjugate as in claim 24, characterized in that the molecule or molecules having at least one free thiol function before conjugation are markers.

28. Conjugate as in claim 27, characterized in that the markers are alkaline phosphatase previously modified to include free thiol functions.

29. In a method of using a conjugate for in vitro diagnostic methods of diseases involving recognition of a ligand-antiligand pair, the improvement comprising using the conjugate of claim 24 for the in vitro diagnostic methods.

* * * * *